(12) United States Patent
Kumar et al.

(10) Patent No.: US 9,659,335 B2
(45) Date of Patent: May 23, 2017

(54) SAMPLE MANAGEMENT FOR A SALES CALL

(75) Inventors: Darshan Kumar, San Ramon, CA (US); Ambili Sudhi, Bangalore (IN); Govindraja Achar, Bangalore (IN); Pankesh Jhaveri, North Brunswick, NJ (US); Harish Kumar, Bangalore (IN); Pinjari Allavali, Karnataka (IN); Walter Back, San Jose, CA (US)

(73) Assignee: Oracle International Corporation, Redwood Shores, CA (US)

( * ) Notice: Subject to any disclaimer, the term of this patent is extended or adjusted under 35 U.S.C. 154(b) by 96 days.

(21) Appl. No.: 12/362,406

(22) Filed: Jan. 29, 2009

(65) Prior Publication Data

US 2010/0191559 A1    Jul. 29, 2010

(51) Int. Cl.
*G06Q 50/22* (2012.01)
*G06Q 10/06* (2012.01)
*G06Q 30/02* (2012.01)

(52) U.S. Cl.
CPC ....... *G06Q 50/22* (2013.01); *G06Q 10/06398* (2013.01); *G06Q 30/02* (2013.01)

(58) Field of Classification Search
CPC ... G06Q 50/22; G06Q 10/06398; G06Q 30/02
USPC ......................................................... 705/2
See application file for complete search history.

(56) References Cited

U.S. PATENT DOCUMENTS

| | | | |
|---|---|---|---|
| 6,055,507 A | 4/2000 | Cunningham | |
| 6,161,176 A | 12/2000 | Hunter et al. | |
| 6,178,439 B1 | 1/2001 | Feit | |
| 6,188,401 B1 | 2/2001 | Peyer | |
| 6,229,537 B1 | 5/2001 | Sobeski et al. | |
| 6,377,993 B1 * | 4/2002 | Brandt ................ G06F 11/0709 707/E17.107 | |
| 6,430,591 B1 | 8/2002 | Goddard | |
| 6,453,302 B1 | 9/2002 | Johnson et al. | |
| 6,523,102 B1 | 2/2003 | Dye et al. | |
| 6,542,595 B1 | 4/2003 | Hemzal | |
| 6,624,831 B1 | 9/2003 | Shahine et al. | |
| 6,630,946 B2 | 10/2003 | Elliott et al. | |
| 6,636,863 B1 | 10/2003 | Friesen | |
| 6,683,943 B2 | 1/2004 | Wuelly | |
| 6,859,780 B1 | 2/2005 | Cunningham | |
| 6,944,829 B2 | 9/2005 | Dando et al. | |
| 6,952,681 B2 | 10/2005 | McQuade et al. | |

(Continued)

OTHER PUBLICATIONS

U.S. Office Action, U.S. Appl. No. 12/363,371, Date: Dec. 7, 2010, pp. 1-17.

(Continued)

*Primary Examiner* — Kevin Flynn
*Assistant Examiner* — Scott Tungate
(74) *Attorney, Agent, or Firm* — Miles & Stockbridge PC

(57) ABSTRACT

Systems and methods are provided that record details of product samples given to a customer. A request to add one or more product sample records is received, and in response, user interface showing product sample information for available product samples is presented. The user interface may include a field for entering a quantity of each product sample given to the customer. One or more product sample records is recorded corresponding to each product sample for which a quantity was entered in the user interface.

20 Claims, 12 Drawing Sheets

(56) References Cited

U.S. PATENT DOCUMENTS

| | | | |
|---|---|---|---|
| 6,963,826 B2 | 11/2005 | Hanaman et al. | |
| 6,990,454 B2 | 1/2006 | McIntosh | |
| 6,996,569 B1* | 2/2006 | Bedell | G06F 17/30412 |
| | | | 707/737 |
| 7,058,890 B2 | 6/2006 | George et al. | |
| 7,107,548 B2 | 9/2006 | Shafron | |
| 7,179,751 B2 | 2/2007 | Smith et al. | |
| 7,219,127 B2 | 5/2007 | Huck et al. | |
| 7,222,305 B2 | 5/2007 | Teplov et al. | |
| 7,240,070 B1 | 7/2007 | Man Cheng et al. | |
| 7,243,336 B2 | 7/2007 | Brockway et al. | |
| 7,249,053 B2 | 7/2007 | Wohlers et al. | |
| 7,406,534 B2 | 7/2008 | Syvanne et al. | |
| 7,467,355 B1 | 12/2008 | Zukowski et al. | |
| 7,590,939 B2 | 9/2009 | Sareen et al. | |
| 7,679,637 B1 | 3/2010 | Kohler | |
| 7,707,513 B2 | 4/2010 | Broda et al. | |
| 7,805,334 B1 | 9/2010 | Huppert | |
| 7,827,481 B1 | 11/2010 | Greenfield | |
| 7,836,403 B2 | 11/2010 | Viswanathan | |
| 7,956,869 B1 | 6/2011 | Gilra | |
| 8,020,083 B1 | 9/2011 | Kembel et al. | |
| 8,229,969 B1 | 7/2012 | Floyd | |
| 2001/0044731 A1 | 11/2001 | Coffman et al. | |
| 2002/0032501 A1 | 3/2002 | Tilles et al. | |
| 2002/0032582 A1 | 3/2002 | Feeney et al. | |
| 2002/0065683 A1 | 5/2002 | Pham et al. | |
| 2002/0133520 A1* | 9/2002 | Tanner | G06F 17/30017 |
| | | | 715/202 |
| 2002/0169795 A1 | 11/2002 | Elliott et al. | |
| 2002/0173990 A1 | 11/2002 | Marasco | |
| 2002/0188513 A1 | 12/2002 | Gil et al. | |
| 2003/0004840 A1 | 1/2003 | Gharavy | |
| 2003/0040953 A1 | 2/2003 | Kasler et al. | |
| 2003/0055713 A1 | 3/2003 | Pinto et al. | |
| 2003/0066032 A1 | 4/2003 | Ramachandran et al. | |
| 2003/0088442 A1 | 5/2003 | Michael et al. | |
| 2003/0123631 A1 | 7/2003 | Moss et al. | |
| 2003/0144857 A1 | 7/2003 | Lacour et al. | |
| 2003/0158947 A1 | 8/2003 | Bloch et al. | |
| 2003/0197366 A1 | 10/2003 | Kusterbeck | |
| 2003/0226111 A1 | 12/2003 | Wirts et al. | |
| 2004/0017397 A1 | 1/2004 | Bach | |
| 2004/0024740 A1 | 2/2004 | McGeorge | |
| 2004/0032431 A1 | 2/2004 | Hymes | |
| 2004/0041841 A1 | 3/2004 | LeMogne | |
| 2004/0056894 A1 | 3/2004 | Zaika et al. | |
| 2004/0113934 A1 | 6/2004 | Kleinman et al. | |
| 2004/0138965 A1 | 7/2004 | Laughlin et al. | |
| 2004/0141004 A1 | 7/2004 | Cabezas et al. | |
| 2004/0141016 A1 | 7/2004 | Fukatsu et al. | |
| 2004/0187127 A1 | 9/2004 | Gondi et al. | |
| 2004/0205343 A1 | 10/2004 | Forth et al. | |
| 2004/0225528 A1 | 11/2004 | Brock | |
| 2004/0255232 A1 | 12/2004 | Hammond et al. | |
| 2005/0039139 A1 | 2/2005 | Schwartz et al. | |
| 2005/0065756 A1 | 3/2005 | Hanaman et al. | |
| 2005/0076330 A1 | 4/2005 | Almgren | |
| 2005/0102192 A1 | 5/2005 | Gerrits et al. | |
| 2005/0108044 A1 | 5/2005 | Koster | |
| 2005/0108295 A1 | 5/2005 | Karimisetty et al. | |
| 2005/0125806 A1 | 6/2005 | Bussler et al. | |
| 2005/0198220 A1 | 9/2005 | Wada | |
| 2006/0010397 A1 | 1/2006 | Laffey | |
| 2006/0069785 A1 | 3/2006 | Barrett | |
| 2006/0074775 A1 | 4/2006 | Roman et al. | |
| 2006/0085449 A1 | 4/2006 | Sattler et al. | |
| 2006/0122971 A1 | 6/2006 | Berg et al. | |
| 2006/0129432 A1 | 6/2006 | Choi et al. | |
| 2006/0136843 A1 | 6/2006 | Shafron | |
| 2006/0190809 A1 | 8/2006 | Hejna, Jr. | |
| 2006/0247968 A1 | 11/2006 | Kadry | |
| 2006/0293930 A1 | 12/2006 | Rodgers et al. | |
| 2006/0294468 A1 | 12/2006 | Sareen et al. | |
| 2007/0016869 A1 | 1/2007 | Mukundan | |
| 2007/0016876 A1 | 1/2007 | Schultz | |
| 2007/0186167 A1 | 8/2007 | Anderson | |
| 2007/0192192 A1 | 8/2007 | Haberman et al. | |
| 2007/0192410 A1 | 8/2007 | Liversidge et al. | |
| 2007/0203785 A1 | 8/2007 | Thompson et al. | |
| 2007/0203851 A1 | 8/2007 | Sudhi | |
| 2007/0220039 A1 | 9/2007 | Waldman et al. | |
| 2007/0226027 A1 | 9/2007 | Chang | |
| 2007/0226082 A1 | 9/2007 | Leal | |
| 2007/0283287 A1 | 12/2007 | Taylor et al. | |
| 2007/0294612 A1 | 12/2007 | Drucker et al. | |
| 2008/0075251 A1 | 3/2008 | Jefferson et al. | |
| 2008/0103821 A1* | 5/2008 | Cerbone | G06Q 50/22 |
| | | | 705/2 |
| 2008/0103856 A1 | 5/2008 | Ciszkowski | |
| 2008/0109286 A1 | 5/2008 | Johnson et al. | |
| 2008/0114709 A1 | 5/2008 | Dixon et al. | |
| 2008/0126179 A1 | 5/2008 | Norfolk et al. | |
| 2008/0134077 A1 | 6/2008 | Cheng et al. | |
| 2008/0140449 A1 | 6/2008 | Hayes | |
| 2008/0172603 A1 | 7/2008 | Agarwal et al. | |
| 2008/0184157 A1 | 7/2008 | Selig | |
| 2008/0195504 A1 | 8/2008 | Wren | |
| 2008/0250433 A1 | 10/2008 | Orton et al. | |
| 2008/0255886 A1 | 10/2008 | Unkefer et al. | |
| 2008/0271059 A1 | 10/2008 | Ott et al. | |
| 2008/0281783 A1 | 11/2008 | Papkoff | |
| 2008/0320509 A1 | 12/2008 | Gustafson et al. | |
| 2009/0024647 A1 | 1/2009 | Hein | |
| 2009/0077170 A1 | 3/2009 | Milburn et al. | |
| 2009/0125850 A1 | 5/2009 | Karstens | |
| 2009/0125907 A1 | 5/2009 | Wen et al. | |
| 2009/0172564 A1 | 7/2009 | Fish | |
| 2009/0210796 A1 | 8/2009 | Bhogal et al. | |
| 2009/0248646 A1 | 10/2009 | Probst et al. | |
| 2009/0249290 A1 | 10/2009 | Jenkins | |
| 2009/0254828 A1 | 10/2009 | Denoue et al. | |
| 2009/0265255 A1 | 10/2009 | Jackson et al. | |
| 2009/0282041 A1 | 11/2009 | Skaria et al. | |
| 2009/0305217 A1 | 12/2009 | Mulcahy et al. | |
| 2009/0327934 A1 | 12/2009 | Serpico et al. | |
| 2010/0037168 A1 | 2/2010 | Thayne et al. | |
| 2010/0049699 A1 | 2/2010 | Benschoter et al. | |
| 2010/0114985 A1 | 5/2010 | Chaudhary et al. | |
| 2010/0151846 A1 | 6/2010 | Vuong | |
| 2010/0161713 A1 | 6/2010 | Gangadharappa et al. | |
| 2010/0332227 A1 | 12/2010 | Melamed et al. | |
| 2012/0030553 A1 | 2/2012 | Delpha | |

OTHER PUBLICATIONS

U.S. Appl. No. 12/363,385, Darshan Kumar.
U.S. Appl. No. 12/362,409, Darshan Kumar.
U.S. Appl. No. 12/363,517, Darshan Kumar.
U.S. Appl. No. 12/362,398, Darshan Kumar.
U.S. Appl. No. 12/362,416, Darshan Kumar.
U.S. Appl. No. 12/363,402, Darshan Kumar.
U.S. Appl. No. 12/363,411, Darshan Kumar.
U.S. Appl. No. 12/363,371, Darshan Kumar.
Oracle, "Siebel Mobile Solutions," Oracel Data Sheet, 2007, pp. 1-4.
U.S. Office Action, U.S. Appl. No. 12/363,411, dated Mar. 31, 2011.
U.S. Office Action, U.S. Appl. No. 12/363,371, dated Mar. 25, 2011.
Office Action dated Jun. 8, 2011 issued in U.S. Appl. No. 12/362,409.
"Boehringer Inglhein Holland Experiences Significant Increase in Customer Satisfaction in 12 Months Using Siebel Pharma", Business Wire, NY p. 1, Mar. 2004.
"Business Update; CSSC Completes Siebel Systems Validations for Three Pharmaceutical Firms", Health and Medicine Week, Atlanta, p. 346, May 25, 2006.
"Demantra Introduces Demantra Suite 4.0—Software That Offers Ten Times Return on Investment by Managing Product Demand"; Business Wire, NY, p. 1, Apr. 2, 2001.
"iAnywhere Prescribes Mobile Technology to Eli Lily's Italian Sales Team", PR Newswire, NY, p. 1, Mar. 22, 2004.

(56) References Cited

OTHER PUBLICATIONS

"Novo Nordisk Expands Siebel Pharma Deployment to Optimize European Sales Effectiveness", Business Wire, NY, p. 1, May 2003.
Oracle Licenses CIC's of eSignature Technology for Siebel Handheld for Pharma and Siebel Handheld for Service, PR Newswire, NY, Jan. 9, 2007.
Phoenix Territory Management System, incorporated by reference into Cerbone et al., U.S. Patent Application Publication No. 2008/0103821, publication date May 1, 2008.
Siebel Life Sciences Guide, Version 7.8, Rev. A Sep. 2005 pp. 1-108 http://www.erp100.com/document/Siebel/Version7.8/B31104_01/books/PDF/LSSIA.pdf.
Siebel Pharma Dynamic Sales for Pharmaceutical Biotechnology Companies, An Oracle White Paper, Customer Relationship Management and Business Analytics, Jun. 2006 http://www.oracle.com/us/industries/life-sciences/042929.pdf.
Siebel Pharma Handheld Guide, Version 7-7, Siebel Systems, Jun. 2004.
Siebel Pharma Handheld Guide, Version 7-8, May 2005 http://download.oracle.com/docs/cd/B31104_02/books/PDF/HHPharm.pdf.
Siebel Systems Inc., Siebel Enterprise Applications, Siebel Interactive Guide, Siebel 99, Version 5-5, 10PA1-A101-05500, Jun. 1999.
Siebel Life Sciences Guide, Version 7.8, Rev. A Sep. 2005 pp. 109-230 http://www.erp100.com/document/Siebel/Version7.8/B31104_01/books/PDF/LSSIA.pdf.
Siebel Life Sciences Guide, Version 7.8, Rev. A Sep. 2005 pp. 231-358 http://www.erp100.com/document/Siebel/Version7.8/B31104_01/books/PDF/LSSIA.pdf.
Siebel Life Sciences Guide, Version 7.8, Rev. A Sep. 2005 pp. 359-464 http://www.erp100.com/document/Siebel/Version7.8/B31104_01/books/PDF/LSSIA.pdf.
Kunau ("Enterprise Architecture, Life Sciences, and Visualization", Oct. 4, 2006, http://kunau.us/generalinterest/design/macromedia-flex-as-an-interface-builder-for-life-sciences-applications/).
Oracle Siebel Life Sciences Guide, Version 7.7, Rev. C, Jun. 2007.
Oracle Siebel Life Sciences Guide, Version 7.8, Rev. C, May 2008.
Oracle Siebel Pharma Handheld Guide, Version 8.0, Rev. A, May 2007.
Oracle Data Sheet, "Siebel Mobile Solutions," Copyright 2007.
Oracle White Paper, "Oracle CRM for Life Sciences—Closed Loop Marketing Solution for the Pharmaceutical Sales Model," Copyright 2009.
Oracle White Paper, "Siebel Pharma Dynamic Sales Solution," Copyright 2006.
"The Telemarketing Sales Rule", Published by Consumers a Helpful Guide on Sep. 1, 2005, pp. 1 and 2.
"Data Services Made Easy for Adobe Flex Applications", Flex Developer Boot Camp Sep. 23, 2007, Santa Clara, CA., pp. 1-9.
Oracle Quality Implementation Guide, Release 12, Part No. B31579-01, Dec. 2006 http://docs.oracle.com/cd/B34956_01/current/acrobat/120qaig.pdf.
Final Office Action mailed on Sep. 15, 2016 for U.S. Appl. No. 12/363,517.

\* cited by examiner

SAMPLE MANAGEMENT FOR A SALES CALL

FIELD OF THE INVENTION

One embodiment is directed to customer relationship management, and more particularly directed to sample management during a sales call.

BACKGROUND INFORMATION

In recent years, the annual rate of increase among physicians has remained relatively flat while the number of pharmaceutical sales representatives has grown considerably overall, even accounting for recent reductions in field force sizes. As a result, sales call effectiveness has waned in the face of a changing market and physicians' increasingly busy schedules, forcing life sciences organizations to transform their sales and marketing capabilities. Pharmaceutical companies face stiff challenges in terms of completion, cost escalation and reduction in margins, while promoting their products by sending out sales representatives to doctors, hospitals and other medical organizations. Typically the sales representatives, in the few minutes that they get with the audience/doctors, orally explain the complicated details of the medical product and then give handouts, such as presentation material on the product in paper form. A very likely result of such an approach is that after the session the audience would have already forgotten much, depending on the oral presentation skills of the representative, and the handouts most likely be thrown away. Furthermore, the sales representative may not come away with a written or other record of the presentation such as how much time was spent addressing the various details of the product, or what samples were left with the physician.

SUMMARY OF THE INVENTION

One embodiment is a system for recording details of product samples given to a customer. A request to add one or more product sample records is received. The system then retrieves product sample information for available product samples and populates an inventory list with the product sample information in a user interface The user interface includes a field for entering a quantity of each product sample given to the customer. The system then creates one or more product sample records corresponding to each product sample for which a quantity was entered.

BRIEF DESCRIPTION OF THE DRAWINGS

FIG. 3 illustrates example call details user interface ("UI") of the SCM system in accordance with an embodiment;

FIG. 4A illustrates a screenshot of an example UI requiring numerous mouse clicks;

FIG. 4B illustrates another screenshot of an example UI requiring numerous mouse clicks;

FIG. 8 illustrates an example screenshot of a sample details UI of the SCM system in accordance with an embodiment.

DETAILED DESCRIPTION

Embodiments are directed to systems and methods for recording details about sample products left with a customer/physician during a sales call presentation. A sales call management ("SCM") system includes a tabular user interface the presents a sales representative with a list of samples that are on-hand and unexpired. At the end of the sales call, the sales representative is presented with this user interface when they elect to add a record of samples left with the physician. The sales representative adds a quantity to a row corresponding to the sample products that were left with the physician. Accordingly, the sales representative may quickly create an accurate record, and the physician can sign off on it in order to comply with government regulations.

Figure 1:
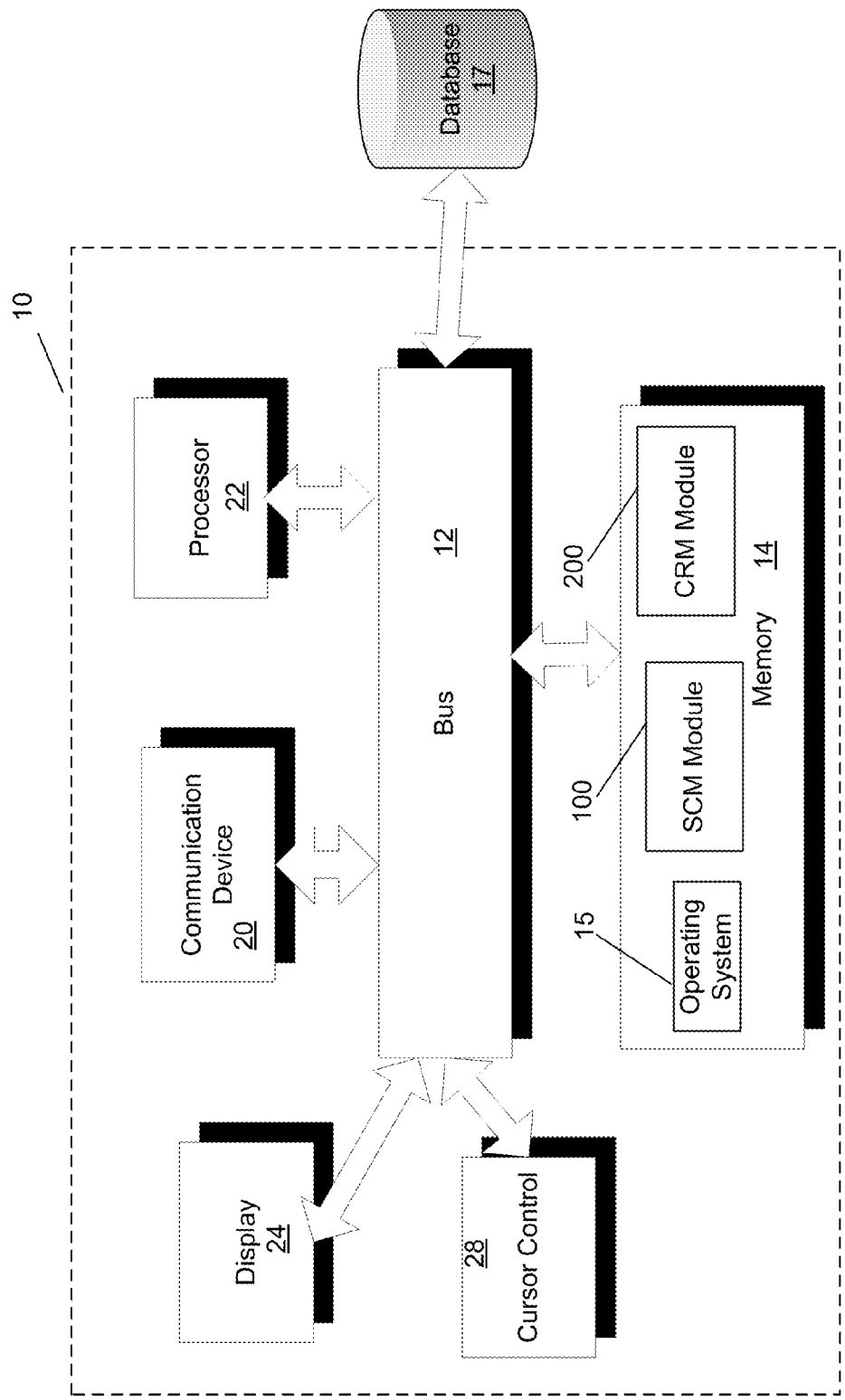
FIG. 1 is a block diagram of a system that can implement a sales call management ("SCM") system in accordance with an embodiment.

FIG. 1 is a block diagram of a system 10 that can implement an embodiment of a SCM system. System 10 includes a bus 12 or other communication mechanism for communicating information, and a processor 22 coupled to bus 12 for processing information. Processor 22 may be any type of general or specific purpose processor. System 10 further includes a memory 14 for storing information and instructions to be executed by processor 22. Memory 14 can be comprised of any combination of random access memory ("RAM"), read only memory ("ROM"), static storage such as a magnetic or optical disk, or any other type of computer readable media. System 10 further includes a communication device 20, such as a network interface card, to provide access to a network. Therefore, a user may interface with system 10 directly, or remotely through a network or any other method.

Computer readable media may be any available media that can be accessed by processor 22 and includes both volatile and nonvolatile media, removable and non-removable media, and communication media. Communication media may include computer readable instructions, data structures, program modules or other data in a modulated data signal such as a carrier wave or other transport mechanism and includes any information delivery media.

Processor 22 is further coupled via bus 12 to a display 24, such as a Liquid Crystal Display ("LCD"), for displaying information to a user. A cursor control device 28, such as a touch screen, is further coupled to bus 12 to enable a user to interface with system 10. In one embodiment, system 10 is a tablet PC.

In one embodiment, memory 14 stores software modules that provide functionality when executed by processor 22. The modules include an operating system 15 that provides operating system functionality for system 10, and a customer relationship management ("CRM") module 200 that provides enterprise-level applications for customer relationship management. The modules further include a SCM module 100, which is described in greater detail below. System 10 may be coupled to a database 17 for storing additional data.

Figure 2:
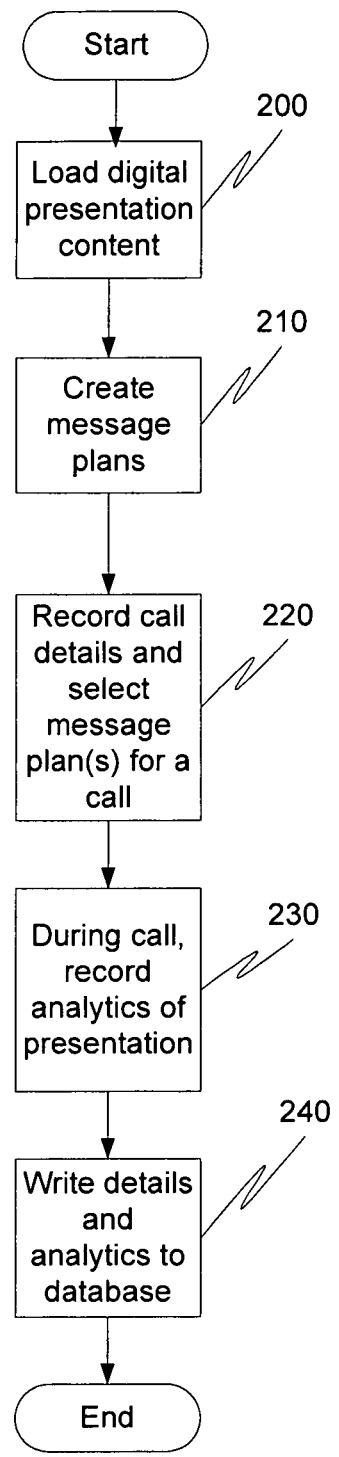
FIG. 2 illustrates a method of providing Sales Call Management and analytics in accordance with an embodiment.

FIG. 2 illustrates a flow diagram of the functionality of SCM module 100 in accordance with an embodiment. In one embodiment, the functionality of the flow diagram of FIG. 2, and FIG. 7 below, is implemented by software stored in memory and executed by a processor. In other embodiments, the functionality may be performed by hardware (e.g., through the use of an application specific integrated circuit ("ASIC"), a programmable gate array ("PGA"), a field programmable gate array ("FPGA"), etc.), or any combination of hardware and software. Initially, digital presentation content is loaded on the SCM system 10 (200). Digital presentation content may be used by brand managers, marketing managers and sales operation managers as a sales communication tool for more effective communication in order to acquire, retain and develop profitable customer relationships and improve marketing and sales effectiveness. Examples of digital presentation content includes presentations in the form of Flash files, PowerPoint files, word documents, movie files, Portable Document files, etc. A "message" refers to a slide, page or segment of a presentation conveying a specific message that managers wish to track.

After loading the digital presentation content on SCM system 10, an administrator or manager may then create a "messaging plan" for the sales representative to use (210). The messaging plan is a sequence of digital presentation content used to deliver the tracked message regarding the product. When a sales representative makes a sales call, a messaging plan is selected on the SCM system 10 and details about the call are entered into the system (220). During the sales call, the SCM system 10 dynamically and automatically collects analytical data such as time spent by the sales representative on each presentation slide and the sequence of slide presentation (230). For example, SCM system may include a timer (not shown) for recording the time spent on each slide or segment of the presentation.

Figure 3:
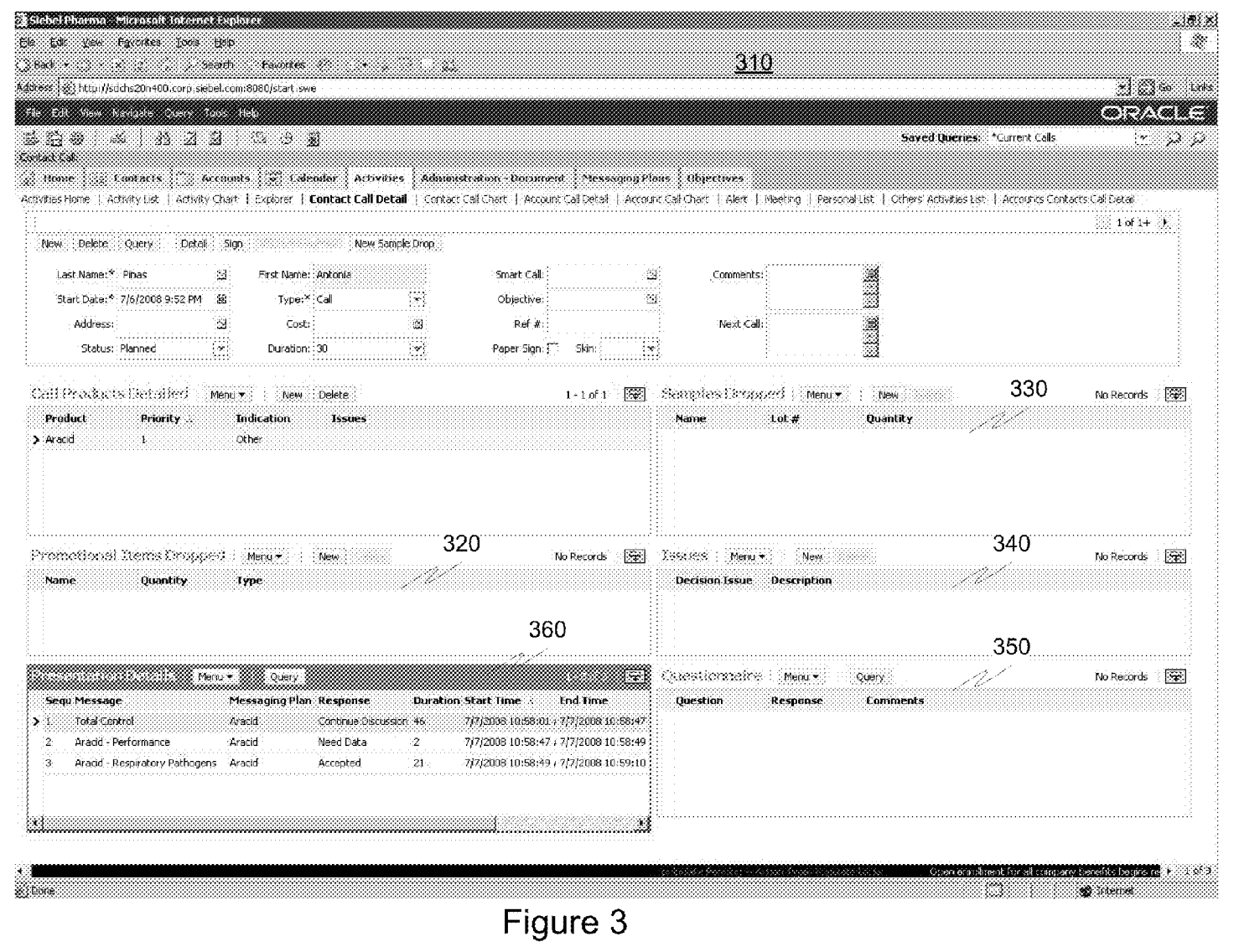

Once the sales presentation is over, the analytical data collected during the session is written back to database 17 (240). After the call, the sales representative may also enter additional details about the sales call such a samples and promotional items left with the doctor or audience, issues about the call, or questionnaires dropped during the call. FIG. 3 illustrates an example screenshot of a UI 310 for SCM system 10 where the sales representative can enter call details in promotional items section 320, samples dropped section 330, issues section 340, and questionnaires section 350. The screenshot UI 310 displays in presentation details section 360 the messages that were presented to the contact in the detailing session, the sequence of presented messages and their parent messaging plans (i.e., the messaging plan to which the messages belong), and duration of presentation of each message. Ultimately, information about the sales call and other sales calls regarding the same product may be used to develop marketing strategies for that product based on the success of the sales calls.

Samples dropped section 330 allows the sales representative to record details about sample and promotional pharmaceutical products (hereinafter "samples") that are left with a physician during a sales call. Government regulations sometime require that the sales representative keep accurate records of what samples are left with the physician, and the physician must "sign off" on the veracity of these records. However, during a sales call a sales representative often has very little time with the physician, and thus it is difficult to keep these records without wasting the physician's time. In a typical CRM application for the pharmaceutical industry, such as Oracle® Life Sciences, data entry for the sample details requires too much time because of the numerous mouse clicks required to navigate various menus and applets.

Figure 4A:
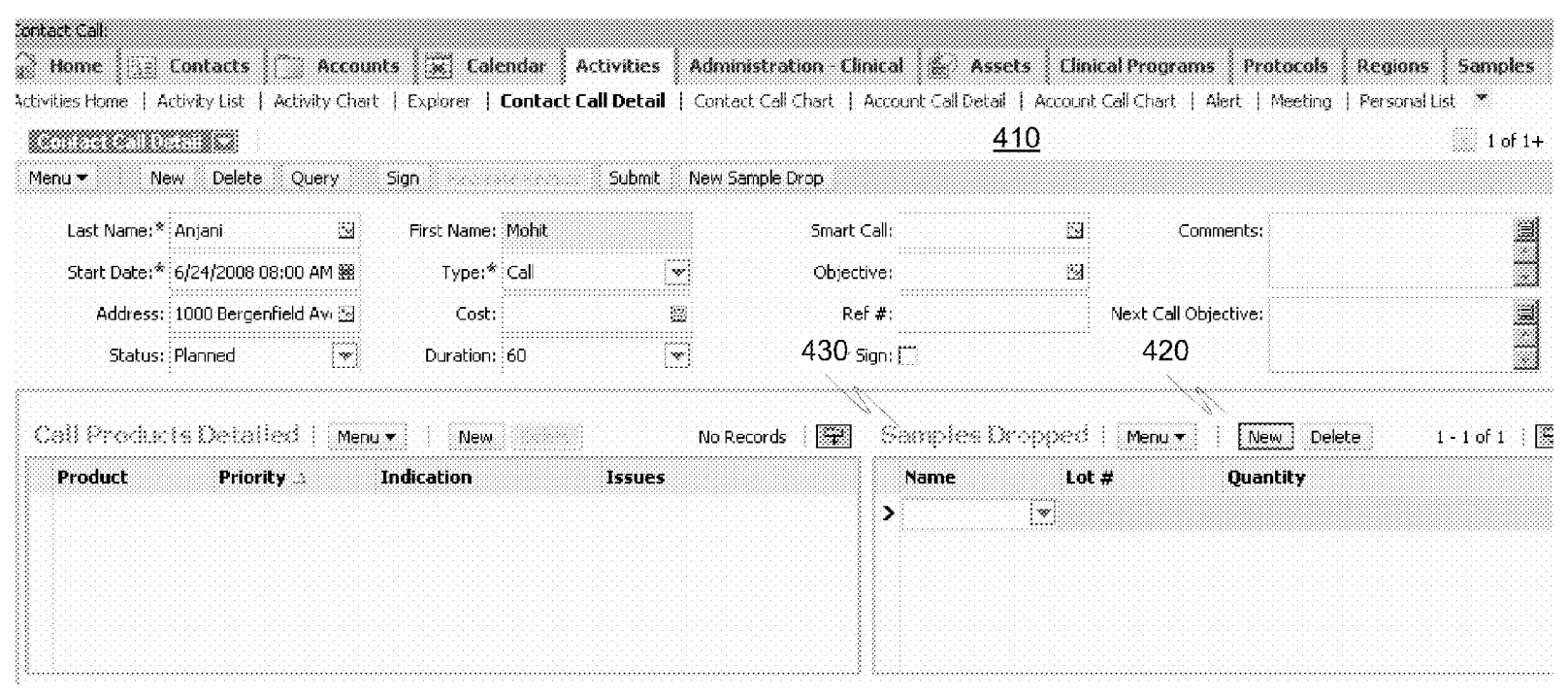
Figure 4B:
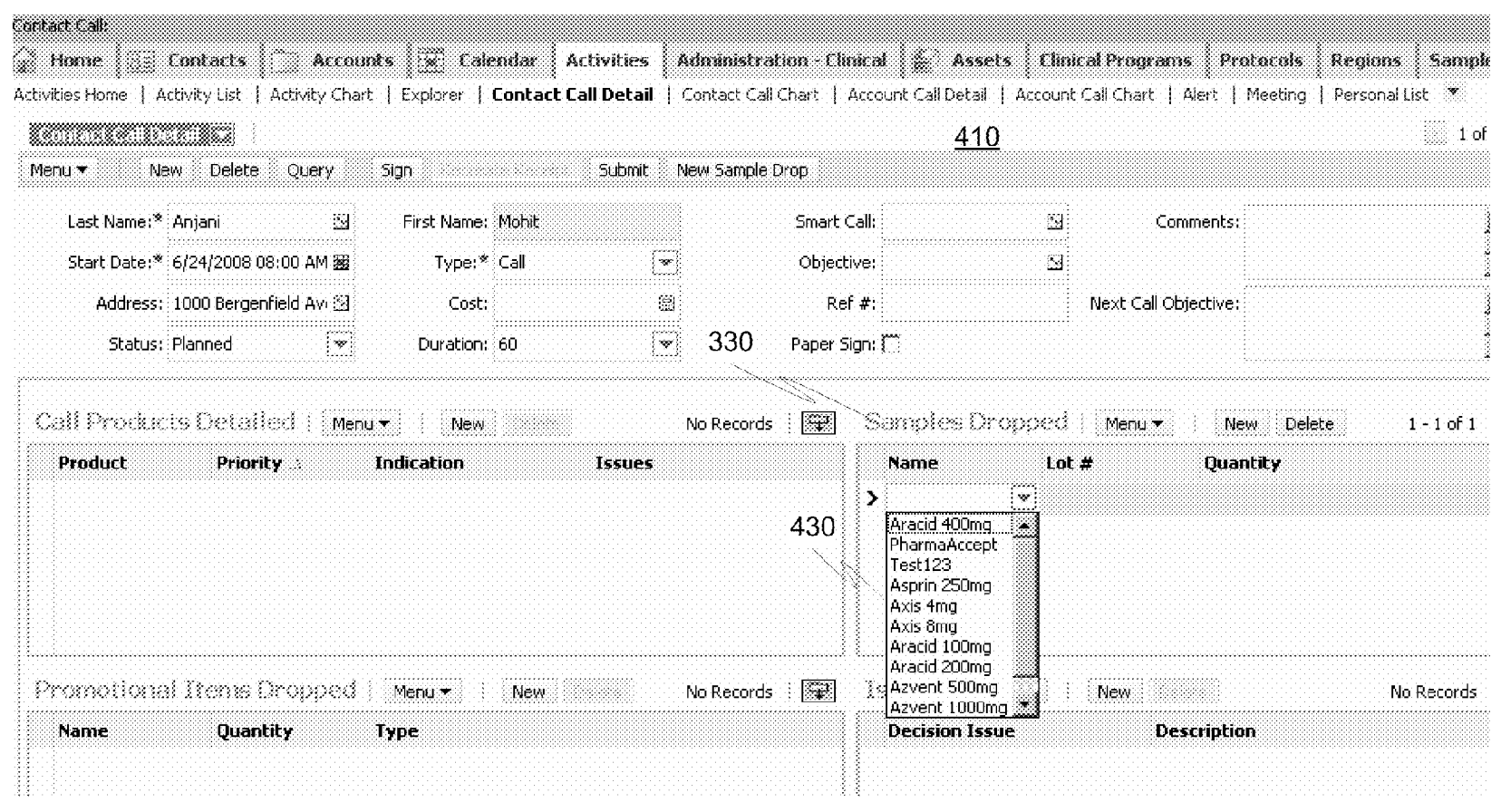
Figure 4C:
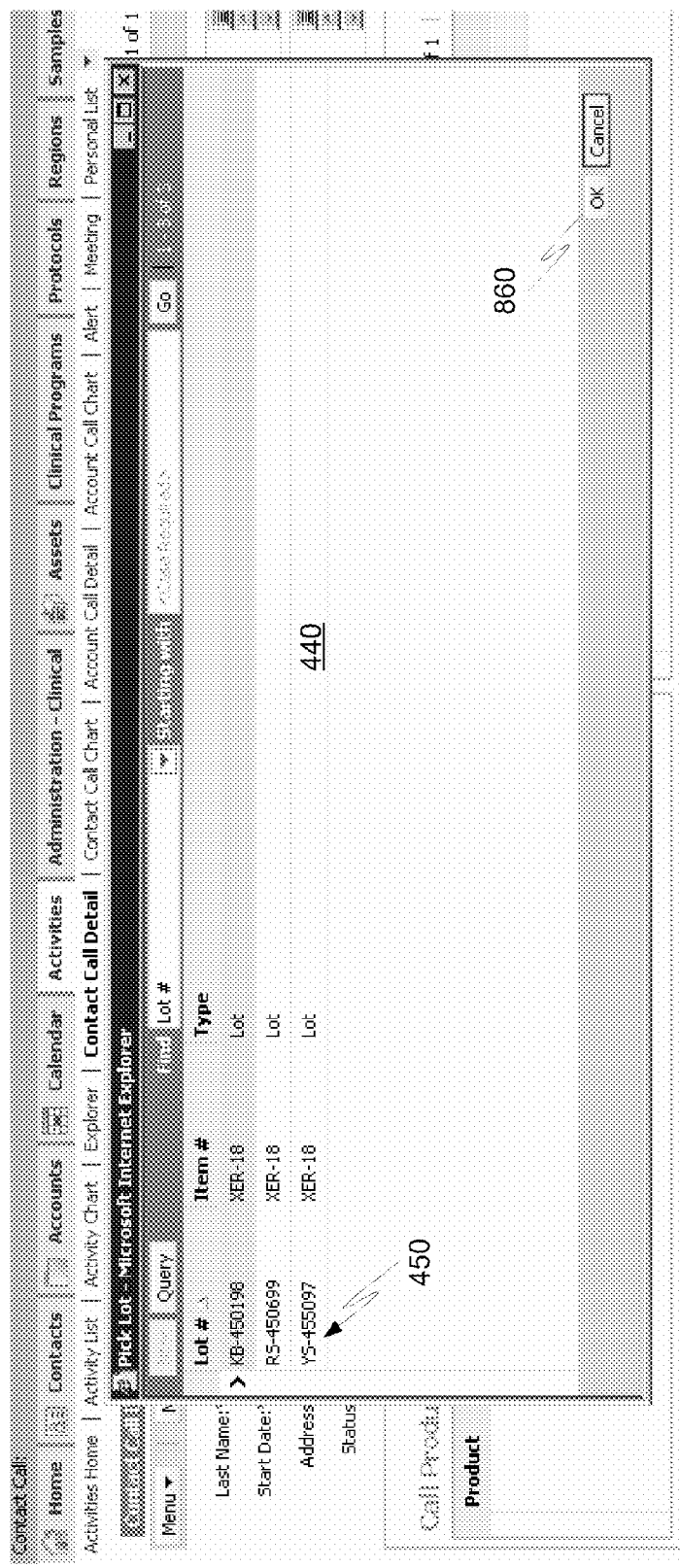
FIG. 4C illustrates yet another screenshot of an example UI requiring numerous mouse clicks.
Figure 4D:
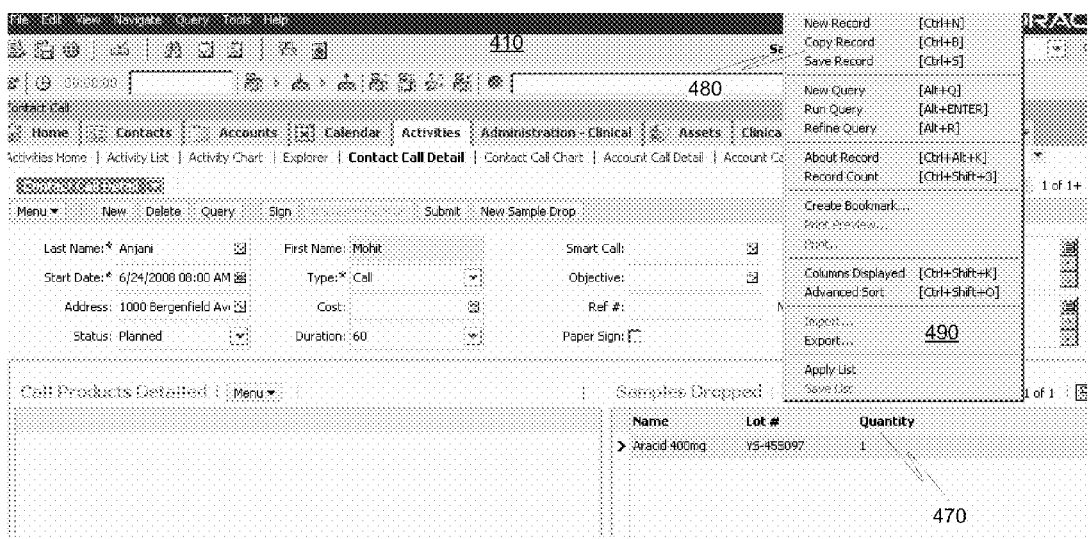
FIG. 4D illustrates yet another screenshot of an example UI requiring numerous mouse clicks.

For example, FIGS. 4A-D illustrates an example screenshot of a UI 410 of a CRM application in the prior art that includes samples dropped section 330. To make an entry in samples dropped section 330, the sales representative first clicks on the "New" button 420 as illustrated in FIG. 4A. Then, as illustrated in FIG. 4B, the sales representative chooses a product from a drop down menu 430. This spawns a popup window 440, as illustrated in FIG. 4C, where the sales representative selects a product lot from the lot number column 450, and then selects the "OK" button 460. The sales representative then enters the quantity of samples dropped in quantity column 470, as illustrated in FIG. 4D, and then selects "Save record" option 480 on popup menu 490. Ultimately, 5 or 6 mouse clicks are necessary to enter details for one dropped sample. Typically, sales representatives leave many samples, thus recording sample details becomes a time consuming process. One workaround is to pre-enter the data before the sales call, or enter the data after the sales call. However, this can lead to inaccurate entries which could result in noncompliance with government regulations.

An embodiment of SCM system 10 includes a virtual business component that communicates with other business components in SCM system 10 to present a sales representative with a unified user interface for an applet that lists products that are available to drop. When a sales representative clicks an "Add" button to add a product, the sales representative is presented with the list and is required to enter only the quantity of the product samples that were left with the physician. SCM system 10 then creates a record for each product sample dropped including the quantity. Accordingly, much less time is required to record the details of samples that were left with the physician. A virtual business component, business component, and applet are explained below.

Business components define a logical entity that associates columns from one or more tables into a single structure. A business component, except a virtual business component, has a base table assigned to it. The base table provides columns of data for use as fields in the business component. That is, fields in the business component map to columns in the base table. For example, a contact business component may map to a contact table. A first name field in the contact business component would map to a first name column in the contact table, a last name field in the contact business component would map to a last name column in the contact table, etc. In addition to including data from base tables, business components can also include data from joined tables. The relationship between the business component and the additional table is defined using a join. A joined table provides rows on a one-to-one basis to the business component as a result of a foreign key relationship between the joined table and the base table of the business component. That is, for every record in the business component (which corresponds to a row in the base table) there can be a corresponding row in the joined table. However, not every record in the base table will have a record in the joined table.

Figure 5:
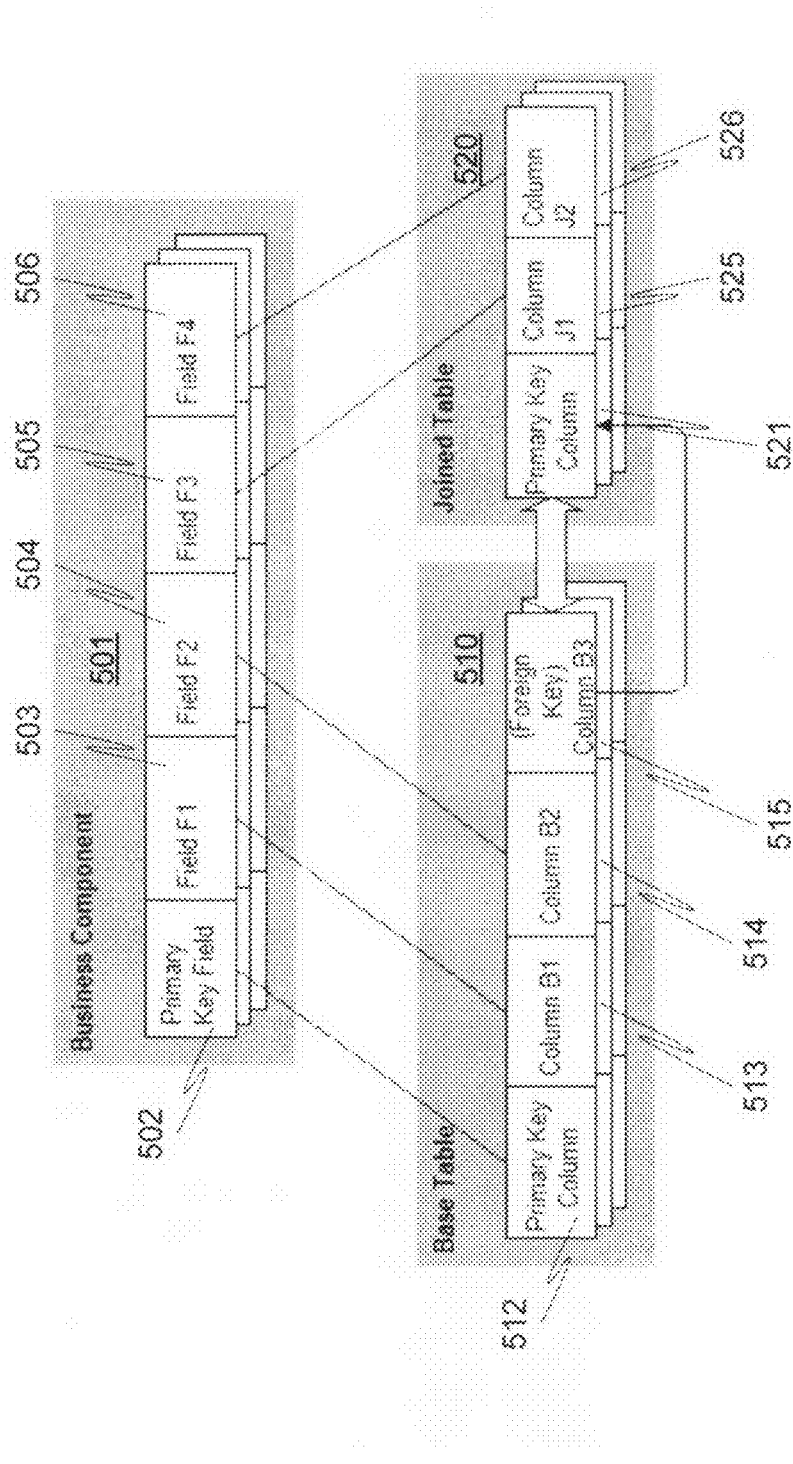
FIG. 5 illustrates an example business component in accordance with an embodiment.

FIG. 5 illustrates an example block diagram of business component 501, its base table 510, and a joined table 520. The mapping between business component 501 and base table 510 is as follows: primary key field 502 maps to primary key column 512, field F1 503 maps to column B1

513, and field F2 504 maps to column B2 514. The mapping between business component 510 and joined table 520 is as follows: field F3 505 maps to column J1 525 and field F4 506 maps to column J2 526. Foreign key column B3 515 refers to primary key column 521, creating the row join. Thus, a business component not only encapsulates data, but is used by the developer to define the behavior of the entity.

Applets are user interface objects that allow users to view, enter, and modify data from a single business component. They occupy a section of a view and include data controls, such as fields, text boxes, and check boxes, as well as other types of controls, such as buttons that invoke methods and ActiveX controls. Applets can be configured to display as forms, lists of records, charts, or hierarchical trees. Applets can be configured to allow data entry for a single record, to provide a scrolling table displaying multiple records, or to display business graphics or a navigation tree. Applets allow users access to the data of a single business component.

Thus, business components provide a layer of wrapping over tables, and applets reference these business components rather than the underlying tables. This design creates convenience (i.e., all associated columns are together in one bundle), developer-friendly naming, and the isolation of the developer role from the system administrator role. Virtual business components provide a code-based mechanism for communicating with multiple business components, as well as external data sources. An applet does not distinguish between a virtual business component and a table-based business component.

Figure 6:
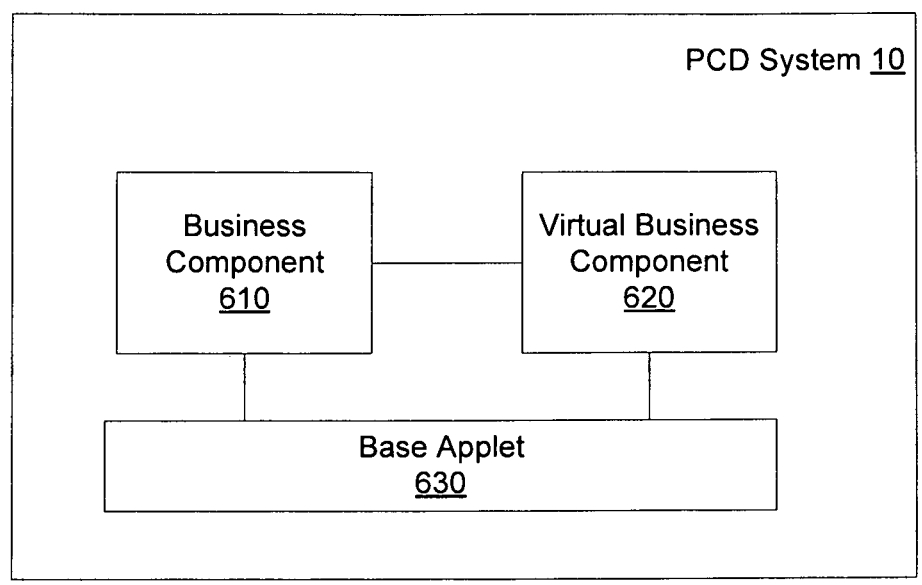
FIG. 6 illustrates a block diagram of the SCM system in accordance with an embodiment.

FIG. 6 illustrates a conceptual block diagram of SCM system 10 including business component 610 and virtual business component 620, and a base applet 630. Base applet 630 may be an interactive detailing session application for SCM system 10, and may have UI 630 as a user interface. Business component 610 is created by joining tables of on-hand inventory (i.e., the actual inventory of the sales representative), original inventory (i.e., the inventory that was allocated to the sales representative by the manufacturer during the last allocation), product lot numbers (i.e., the lot number or batch number of a particular sample), and expiration dates for samples. In an embodiment, business component 610 retrieves the inventory information through CRM modules 200. Business component 610 includes a search facility to filter out, for example, lots of samples that have expired and thus should not be sampled, products where the on-hand quantity is zero, and products that have been flagged to discontinue sampling (e.g., because of pending litigation). These tables may be stored in database 17.

Figure 7:
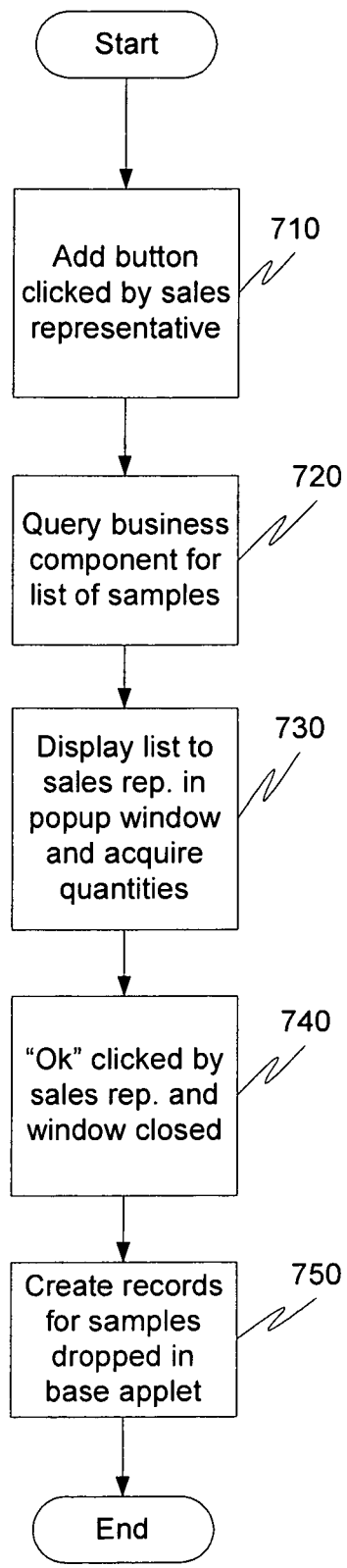
FIG. 7 illustrates a method of recording sample details in accordance with an embodiment.

FIG. 7 illustrates a flow diagram of the functionality of SCM system 10 in accordance with an embodiment. When a sales representative wishes to record details about a sample dropped in base applet 630 by clicking an "Add" button (710), virtual business component 620 loads and queries business component 610 to acquire a list of available products and product lots to sample (720). Virtual business component 620 then presents the list, e.g., via a popup window, to the sales representative and prompts them to enter a quantity for each of the product lots distributed (730). When the sales representative closes the popup window by clicking "OK" (740) the virtual business component creates a record of the product and product lot number in base applet 630 (750).

Figure 8:
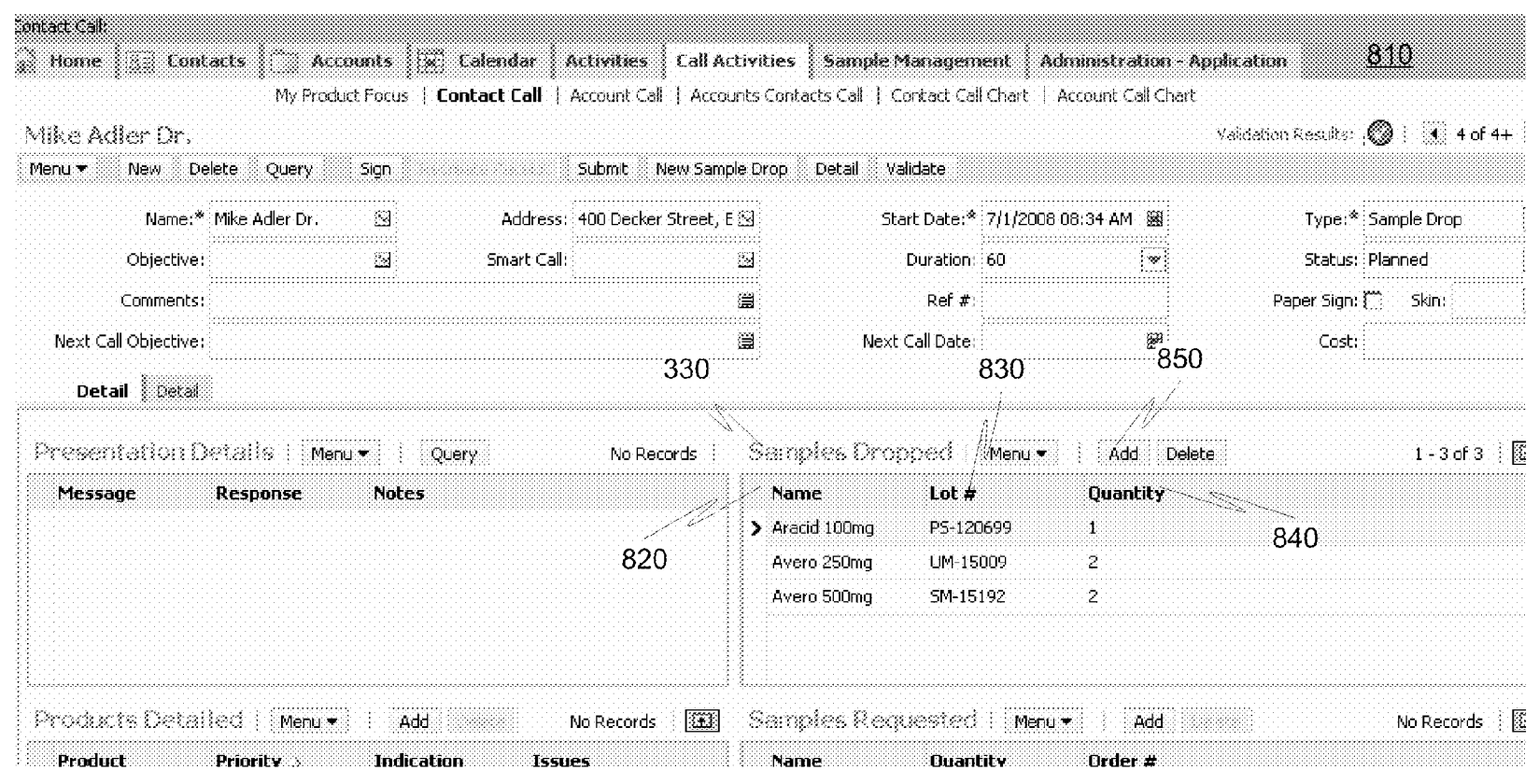
Figure 9:
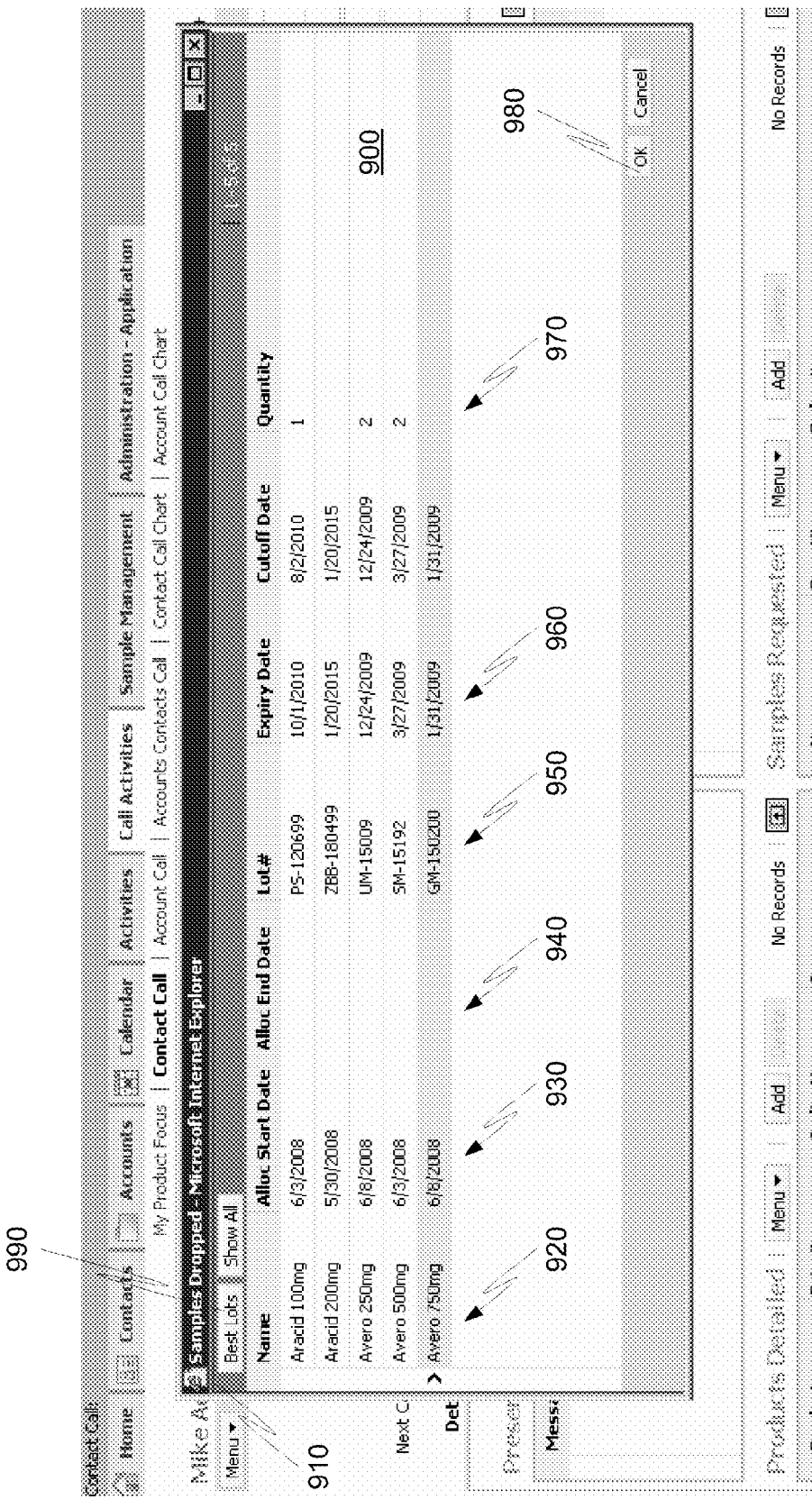
FIG. 9 illustrates another example screenshot of the sample details UI of the SCM system in accordance with an embodiment

FIG. 8 illustrates an example screenshot of UI 810 of base applet 630 in SCM system 10. UI 810 includes samples dropped section 330 as previously discussed. Note that samples dropped section 330 includes details for three samples that were already dropped, including the sample's product name in column 820, product lot number in column 830, and quantity left with the physician in column 840. When a sales representative clicks on "Add" button 850, they are presented with popup window 900 as illustrated in FIG. 9. Popup window 900 includes table 910 of the available products to sample. Table 910 includes product name column 920, allocation start date column 930 indicating the date the samples were given to the sales representative, allocation end date column 940 indicating the date the sales representative should return unused samples, lot number column 950, expiration date column 960, and quantity column 970 in which the sales representative enters the quantity of each product lot that was sampled. When the sales representative clicks "OK" button 980, this data is captured and updated in base applet 630. Popup window 900 further includes best lots button 990 that filters the available products and presents a list of the best product lots based on expiration dates.

The functionality of virtual business component 620 is, in part, achieved by two methods: one for querying other business components and presenting the data to the sales representative, and one for capturing the quantity of sample product lots dropped and updating the records in the base applet 630. Example code for the two methods, LoadCallProducts( ) and UpsertCallProducts( ), are presented below:

```
METHOD NAME:   CSSLSBCVCallProducts::LoadCallProducts
    ErrCode CSSLSBCVCallProducts::LoadCallProducts(BOOL
    bShowAll)
    {
    //Get source Business Component using "User Property" value.
        GetUserProperty(SStext("Source BusComp"), strBusCompName);
        DOCHILD (pBusObj,GetBusComp(strBusCompName,
        pPickListBusComp));
        //Query this Business Component (BC) to get data populated in
        popup
        //applet. This BC already has joins and search specification to show
        //data.
        DOCHILD (pPickListBusComp, Execute(TRUE));
        DOCHILD (pPickListBusComp, Home( ));
    //For each record, create a record in Virtual BC (it will not create
    //record in physical database) and populate data from source BC
        DO (NewRecord(FALSE));
            for (index = 0; EnumFields (index == 0, strFieldName,
    pField); index++)
            {
                if (pPickListBusComp->FieldValue (strFieldName,
    strFldVal) == OK)
                {
                    DO(SetFieldValue (strFieldName, strFldVal, TRUE,
                    TRUE
    ));
                }
            }
        //Copy quantity from Base applet which were inserted last cycle.
            DOCHILD (pParentBC, SetSearchSpec (strUserProperty,
    strFldVal));
            DOCHILD (pParentBC, Execute(TRUE));
            DOCHILD (pParentBC, Home( ));
            if (pParentBC->CheckActiveRow ( ) == OK)
            {
                DOCHILD(pParentBC, FieldValue
    (strUserProperty,strQty));
                DO (SetFieldValue(strUserProperty, strQty));
            }
            DO (WriteRecord( ));
    }
METHOD NAME:   CSSLSBCVCallProducts::UpsertCallProducts
    ErrCode CSSLSBCVCallProducts::UpsertCallProducts( )
    {
        GetUserProperty(SStext("Parent BusComp"), strUserProperty);
        DOCHILD
        (GetBusObj( ),GetBusComp(strUserProperty,pParentBC));
```

-continued

```
//For each record in Virtual BC, see if quantity is entered or not
    DO(FieldValue(strQtyField,strQty));
      DO(FieldValue(strUserProperty,strFldVal));
      DOCHILD (pSqlObj, SetSearchSpec (strUserProperty,
        strFldVal));
      DOCHILD (pSqlObj, Execute( ));
//If the strQty = 0 and corresponding record is found in parent
//applet, then it will delete the record
if (strQty.IsEmpty( ) && pSqlObj->Home(&record) == OK)
{
    DOCHILD(pSqlObj,DeleteRecord(&record,TRUE));
}
//If the strQty > 0 then it will Create the record in the parent
//applet
else if (!strQty.IsEmpty( ) && pSqlObj->Home
    (&record) != OK)
{
    DOCHILD(pSqlObj,NewRecord(&record, FALSE));
//For each field in VBC
{
       DO(FieldValue(strUserProperty,strFldVal));
         DOCHILD(pSqlObj, SetFieldValue(strUserProperty,
strFldVal));
}
    DOCHILD(pSqlObj,WriteRecord(&stmtArray));
}
//If the quantity for existed record is modified then it will
//modify the record in the Parent applet
else if (!strQty.IsEmpty( ))
{
    DOCHILD (pSqlObj, UpdateRecord(&record));
    DO(FieldValue(strUserProperty,strFldVal));
    DOCHILD(pSqlObj,FieldValue(&record,strUserProperty,
strParentFieldVal));
       if (SSstrcmp(strParentFieldVal,strFldVal)!= 0)
       {
           DOCHILD(pSqlObj, SetFieldValue(strUserProperty,
strFldVal));
           bRecordchanged =TRUE;
       }
    }
    if(bRecordchanged)
    {
       DOCHILD(pSqlObj,WriteRecord(&stmtArray));
    }
   }
  }
//Commit all SQL transactions in one action
  if (stmtArray.GetNumSqlStmts( )>0)
  {
    DOCHILD(pSqlObj,WriteRecordArray(stmtArray));
    DOCHILD(pSqlObj,FinishWriteRecord(FALSE));
    stmtArray.Empty( );
  }
 }
```

As disclosed, SCM system 10 includes a virtual business component that queries other business components to build a list of product samples that are on-hand and unexpired. The SCM system 10 then presents this list to the sales representative, who can quickly enter quantity information for the product sample lots that were are left with the physician. Accordingly, SCM system 10 provides faster and more efficient sample detailing by allowing the multiple record entries at the same time, reducing the number of mouse clicks required to record an entry, and ensuring more accurate records and thus better government compliance.

Some embodiments of the invention have been described as computer-implemented processes. It is important to note, however, that those skilled in the art will appreciate that the mechanisms of the invention are capable of being distributed as a program product in a variety of forms. The foregoing description of example embodiments is provided for the purpose of illustrating the principles of the invention, and not in limitation thereof, since the scope of the invention is defined solely by the appended claims.

What is claimed is:

1. A method, implemented by a processor, for recording details of product samples given to a customer, comprising:
   displaying, using an applet, a first window within a user interface, the first window including a customer information section, a presentation section and a samples dropped section including a selectable add samples interface element;
   during a presentation of digital content to an audience, automatically collecting analytical data including at least one metric that measures a feature of the presentation during the presentation, and, after the presentation of digital content is completed, writing the analytical data to a database;
   in response to receiving a selection of the add samples interface element:
      retrieving, using a virtual business component, product sample information for available product samples from a plurality of business components, the product sample information including a product name, a product lot number and an expiration date, each business component defining a logical entity that associates columns from a plurality of tables stored within the database that contain at least a portion of the product sample information into a single structure, the virtual business component including a code-based entity that communicates with the plurality of business components and the applet, and
      displaying, using the applet, a second window within the user interface, the second window including a list of product lots based on the product sample information retrieved by the virtual business component, a selectable best lots interface element and a selectable update data interface element, the list of product lots including a product name, a product lot number, an expiration date and a field for entering a quantity of each product sample given to the customer;
   in response to receiving a selection of the best lots interface element:
      filtering, using the virtual business component, the list of product lots based on expiration date to create a list of best product lots, and
      displaying, using the applet, the list of best product lots in the second window of the user interface; and
   in response to receiving a selection of the update data interface element:
      capturing, using the virtual business component, a quantity of each product sample given to the customer from the list of best product lots,
      creating, using the virtual business component, a product sample record for each product sample given to the customer, the product sample record including a product name, a product lot number and a quantity, and
      recording, using the virtual business component, the product sample records in the database.

2. The method of claim 1, wherein a plurality of product sample records are recorded at substantially the same time.

3. The method of claim 1, wherein the product samples are pharmaceutical samples.

4. The method of claim 3, wherein the product sample record includes a name of the customer to which the product sample was given.

5. The method of claim 4, wherein the customer is a physician.

6. The method of claim 5, further comprising acquiring a signature from the physician verifying that he received one or more product samples.

7. The method of claim 1, wherein the digital content includes a plurality of presentation slides, and the at least one metric includes at least one of a time spent on each presentation slide or a sequence of slide presentation.

8. A non-transitory computer-readable medium having instructions stored thereon that, when executed by a processor, cause the processor to record details of product samples given to a customer by:

displaying, using an applet, a first window within a user interface, the first window including a customer information section, a presentation section and a samples dropped section including a selectable add samples interface element;

during a presentation of digital content to an audience, automatically collecting analytical data including at least one metric that measures a feature of the presentation during the presentation, and, after the presentation of digital content is completed, writing the analytical data to a database;

in response to receiving a selection of the add samples interface element:

retrieving, using a virtual business component, product sample information for available product samples from a plurality of business components, the product sample information including a product name, a product lot number and an expiration date, each business component defining a logical entity that associates columns from a plurality of tables stored within the database that contain at least a portion of the product sample information into a single structure, the virtual business component including a code-based entity that communicates with the plurality of business components and the applet, and displaying, using the applet, a second window within the user interface, the second window including a list of product lots based on the product sample information retrieved by the virtual business component, a selectable best lots interface element and a selectable update data interface element, the list of product lots including a product name, a product lot number, an expiration date and a field for entering a quantity of each product sample given to the customer;

in response to receiving a selection of the best lots interface element:

filtering, using the virtual business component, the list of product lots based on expiration date to create a list of best product lots, and displaying, using the applet, the list of best product lots in the second window of the user interface; and in response to receiving a selection of the update data interface element:

capturing, using the virtual business component, a quantity of each product sample given to the customer from the list of best product lots, creating, using the virtual business component, a product sample record for each product sample given to the customer, the product sample record including a product name, a product lot number and a quantity, and recording, using the virtual business component, the product sample records in the database.

9. The computer-readable medium of claim 8, wherein a plurality of product sample records are recorded at substantially the same time.

10. The computer-readable medium of claim 8, wherein the product samples are pharmaceutical samples.

11. The computer-readable medium of claim 10, wherein the product sample record includes a name of the customer to which the product sample was given.

12. The computer-readable medium of claim 11, wherein the customer is a physician.

13. The computer-readable medium of claim 12, further comprising acquiring a signature from the physician verifying that he received one or more product samples.

14. The computer-readable medium of claim 8, wherein the digital content includes a plurality of presentation slides, and the at least one metric includes at least one of a time spent on each presentation slide or a sequence of slide presentation.

15. A system for recording details of product samples given to a customer, comprising:

a display;
a memory; and
a processor, coupled to the memory and the display, configured to:

display, using an applet, a first window within a user interface, the first window including a customer information section, a presentation section and a samples dropped section including a selectable add samples interface element;

during a presentation of digital content to an audience, automatically collect analytical data including at least one metric that measures a feature of the presentation during the presentation, and, after the presentation of digital content is completed, write the analytical data to a database;

in response to receiving a selection of the add samples interface element:

retrieve, using a virtual business component, product sample information for available product samples from a plurality of business components, the product sample information including a product name, a product lot number and an expiration date, each business component defining a logical entity that associates columns from a plurality of tables stored within the database that contain at least a portion of the product sample information into a single structure, the virtual business component including a code-based entity that communicates with the plurality of business components and the applet, and display, using the applet, a second window within the user interface, the second window including a list of product lots based on the product sample information retrieved by the virtual business component, a selectable best lots interface element and a selectable update data interface element, the list of product lots including a product name, a product lot number, an expiration date and a field for entering a quantity of each product sample given to the customer;

in response to receiving a selection of the best lots interface element:

filter, using the virtual business component, the list of product lots based on expiration date to create a list of best product lots, and display, using the applet, the list of best product lots in the second window of the user interface; and in response to receiving a selection of the update data interface element:

capture, using the virtual business component, a quantity of each product sample given to the customer from the list of best product lots, create, using the virtual business component, a product sample record for each product sample given to the customer, the product sample record including a product name, a product lot number and a quantity, and record, using the virtual business component, the product sample records in the database.

16. The system of claim 15, wherein the product samples are pharmaceutical samples.

17. The system of claim 15, wherein a plurality of product sample records are recorded at substantially the same time.

18. The system of claim 16, wherein the product sample record includes a name of the customer to which the product sample was given.

19. The system of claim 18, wherein the customer is a physician.

20. The system of claim 19, further comprising acquiring a signature from the physician verifying that he received one or more product samples.

* * * * *

UNITED STATES PATENT AND TRADEMARK OFFICE
CERTIFICATE OF CORRECTION

PATENT NO. : 9,659,335 B2
APPLICATION NO. : 12/362406
DATED : May 23, 2017
INVENTOR(S) : Kumar et al.

Page 1 of 1

It is certified that error appears in the above-identified patent and that said Letters Patent is hereby corrected as shown below:

On the Title Page

On page 2, Column 2, under Other Publications, Line 9, delete "Oracel" and insert -- Oracle --, therefor.

On page 2, Column 2, under Other Publications, Line 15, delete "Inglhein" and insert -- Ingelheim --, therefor.

In the Specification

In Column 1, Line 44, delete "interface The" and insert -- interface. The --, therefor.

In Column 2, Line 12, after "embodiment" insert -- . --.

Signed and Sealed this
Fifteenth Day of May, 2018

Andrei Iancu
*Director of the United States Patent and Trademark Office*